(12) United States Patent
LaChapelle et al.

(10) Patent No.: US 8,876,042 B2
(45) Date of Patent: Nov. 4, 2014

(54) INTEGRATED NACELLE ASSEMBLY

(75) Inventors: Donald George LaChapelle, Cincinnati, OH (US); Christopher Charles Glynn, Lawrenceburg, IN (US); Donald Lee Gardner, West Chester, OH (US); Stephen Craig Mitchell, West Chester, OH (US); Mullahalli Venkataramaniah Srinivas, Mason, OH (US); Edward Atwood Rainous, Cincinnati, OH (US); David Lance Pennekamp, Hamilton, OH (US)

(73) Assignee: General Electric Company, Schenectady, NY (US)

( * ) Notice: Subject to any disclaimer, the term of this patent is extended or adjusted under 35 U.S.C. 154(b) by 1143 days.

(21) Appl. No.: 12/827,801

(22) Filed: Jun. 30, 2010

(65) Prior Publication Data
US 2011/0146230 A1    Jun. 23, 2011

Related U.S. Application Data

(60) Provisional application No. 61/288,527, filed on Dec. 21, 2009.

(51) Int. Cl.
*B64D 27/00* (2006.01)
*F02C 7/20* (2006.01)
*B64D 27/18* (2006.01)
*B64D 27/26* (2006.01)

(52) U.S. Cl.
CPC .............. *B64D 27/26* (2013.01); *B64D 27/18* (2013.01); *B64D 2027/268* (2013.01); *B64D 2027/266* (2013.01); *B64D 2027/264* (2013.01)
USPC .............................................. 244/54; 60/796

(58) Field of Classification Search
USPC ............ 60/53 R, 54, 796–797; 248/554–557; 244/53 R, 54
See application file for complete search history.

(56) References Cited

U.S. PATENT DOCUMENTS

| | | | |
|---|---|---|---|
| 4,037,809 A | * | 7/1977 | Legrand ........................ 244/54 |
| 4,458,863 A | * | 7/1984 | Smith ............................. 244/54 |

(Continued)

FOREIGN PATENT DOCUMENTS

CN    101522524    9/2009

OTHER PUBLICATIONS

Unofficial English translation of Office Action issued in connection with MX Application No. MX/a/2010/014247, Nov. 23, 2012.

(Continued)

*Primary Examiner* — Gerald L Sung
(74) *Attorney, Agent, or Firm* — General Electric Company; Pamela A. Kachur

(57) ABSTRACT

An assembly includes a unitary nacelle structure and an integrated fan housing for a gas turbine engine assembly. The unitary nacelle structure includes an inlet region and a fan cowl region, and is configured to at least partially circumscribe the integrated fan housing. The integrated fan housing comprises an integral composite structure and includes a fan case sized and configured for encircling a fan blade assembly of an associated gas turbine engine, a fan hub, and a plurality of fan outlet guide vanes. The unitary nacelle structure cooperates with the integrated fan housing to transfer static and dynamic loads directly to a support structure, rather than through the engine core, to minimize backbone bending.

12 Claims, 4 Drawing Sheets

(56) References Cited

U.S. PATENT DOCUMENTS

| | | | |
|---|---|---|---|
| 4,471,609 A * | 9/1984 | Porter et al. | 60/797 |
| 5,226,789 A | 7/1993 | Donges | |
| 2007/0201984 A1 * | 8/2007 | Liston | 416/230 |
| 2007/0267539 A1 | 11/2007 | Bulin | |
| 2008/0072571 A1 * | 3/2008 | Beardsley et al. | 60/226.2 |
| 2008/0073461 A1 | 3/2008 | Guibert et al. | |
| 2009/0090096 A1 * | 4/2009 | Sheridan | 60/226.3 |
| 2010/0284806 A1 | 11/2010 | Vauchel et al. | |

OTHER PUBLICATIONS

Office Action issued in connection with MX Application No, MX/a/2010/014247, Nov. 23, 2012.

Chinese First Examination Office Action dated Jan. 24, 2014 in corresponding Chinese Patent Application No. 201010620934.7.

* cited by examiner

US 8,876,042 B2

INTEGRATED NACELLE ASSEMBLY

CROSS REFERENCE TO RELATED APPLICATIONS

This Application claims priority and benefit of U.S. Provisional Patent Application Ser. No. 61/288,527 filed Dec. 21, 2009, the disclosure of which is incorporated herein by reference in its entirety.

BACKGROUND OF THE INVENTION

This invention relates generally to integrated composite structures in a gas turbine engine assembly, and more specifically to a nacelle assembly comprising integrated composite structures operable to transfer loads to a pylon support structure and not through a core engine.

In the art, a gas turbine engine assembly may be mounted in supported connection with an associated aircraft through a pylon or structural component through which loads may be transferred from the engine to the aircraft. Additionally, some load, such as inlet lift loads may be reacted through the engine core, resulting in engine backbone bending.

Accordingly, it would be desirable to provide simpler, more lightweight structures to support an engine assembly which transmits forces directly to a support member to minimize backbone bending. There is also a need for accessibility to the engine core for maintenance or replacement. Further, it is desirable to provide adequate space for various components and accessories for the gas turbine engine assembly.

BRIEF DESCRIPTION OF THE INVENTION

The above-mentioned need or needs may be met by exemplary embodiments that provide an assembly including a unitary nacelle structure and an integrated fan housing in supported connection with the nacelle structure. An exemplary nacelle structure is configured to circumscribe at least a portion of an associated gas turbine engine and to direct an airstream to a fan of the gas turbine engine. The exemplary structure includes an inlet region and a fan cowl region. An exemplary integrated fan housing comprises a composite structure and includes a fan case sized and configured for encircling a fan blade assembly of an associated gas turbine engine, a fan hub, and a plurality of fan outlet guide vanes.

Another exemplary embodiment is directed to an assembly including an integrated fan housing comprising a composite structure and including a fan case defining a generally cylindrical body being sized and configured for encircling a fan blade assembly of an associated gas turbine engine, a fan hub, and a plurality of fan outlet guide vanes.

BRIEF DESCRIPTION OF THE DRAWINGS

The subject matter which is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
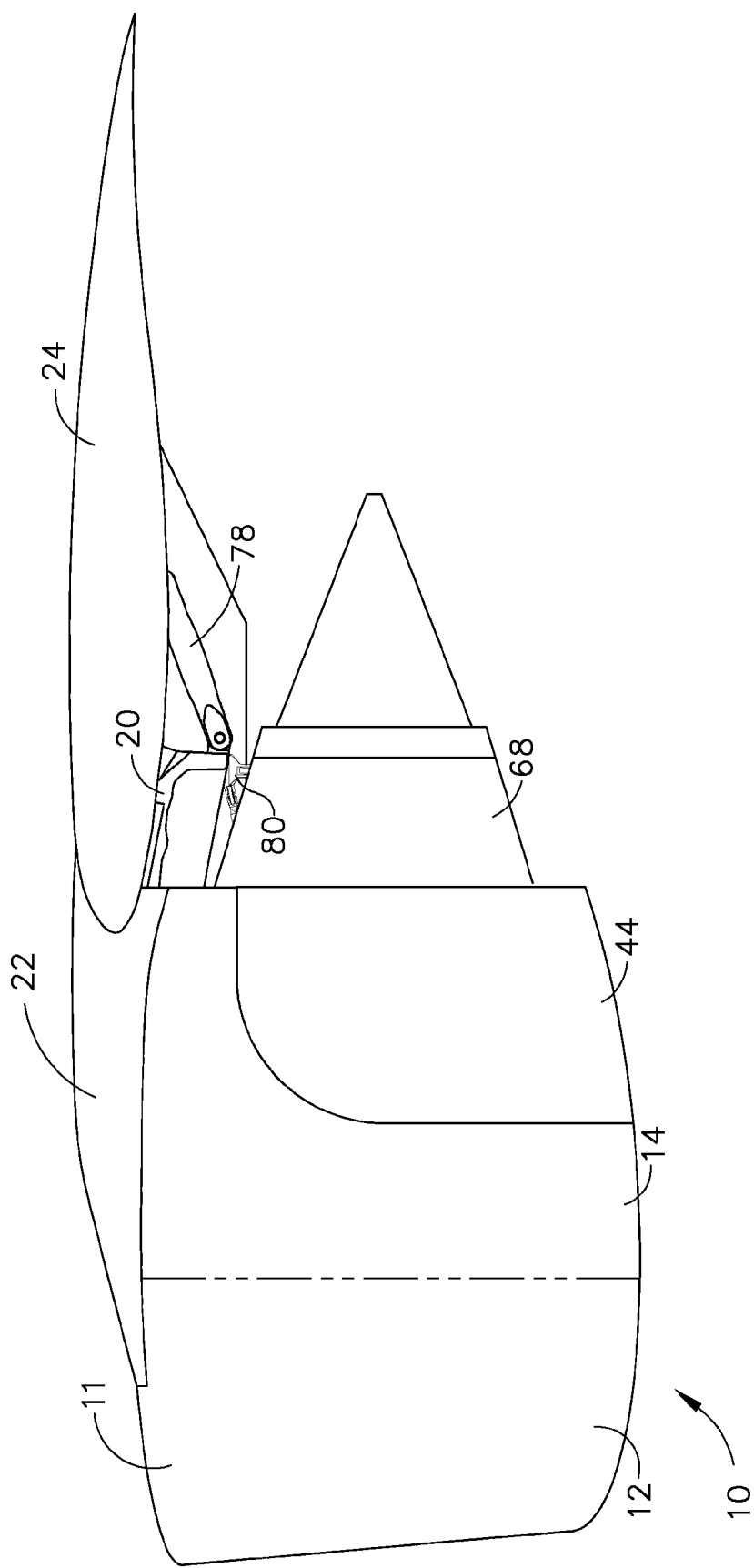
FIG. 1 is a schematic side elevation of an exemplary engine assembly, partially broken away, mounted in supported connection with a wing of an associated aircraft.

Referring to the drawings wherein identical reference numerals denote the same elements throughout the various views, FIG. 1 shows an exemplary engine assembly 10 including a first exemplary integrated structure, termed herein as nacelle structure 11 mounted in supported connection with a support member or strut 20 which is mounted to a wing 24 (partly shown) of an associated aircraft (not shown). In other exemplary embodiments, the support member 20 may be mounted in supported connection with a tail section, or fuselage or the aircraft as is well known in the art.

An exemplary nacelle structure 11 includes an inlet region 12, a fan cowl region 14, and a fairing 22. In operation, the nacelle structure 11 is configured to generally circumscribe a fan assembly, not shown, but understood by those having skill in the art. In exemplary embodiments disclosed herein, the fan thrust load and inlet lift loads are intended to be distributed about the nacelle structure 11 for transfer to the support member 20 and then to the associated aircraft. Transferring loads directly to the support member 20 serves to relieve the backbone bending associated with transferring loads through the engine core. The support member 20 may incorporate a generally conventional design wherein certain attachments, mounts and linkages operate to mount the support member 20 and the gas turbine engine assembly 10 to the associated aircraft. In an exemplary embodiment, the nacelle structure 11 comprises a laminate composite structure formed as a unitary member.

Figure 2:
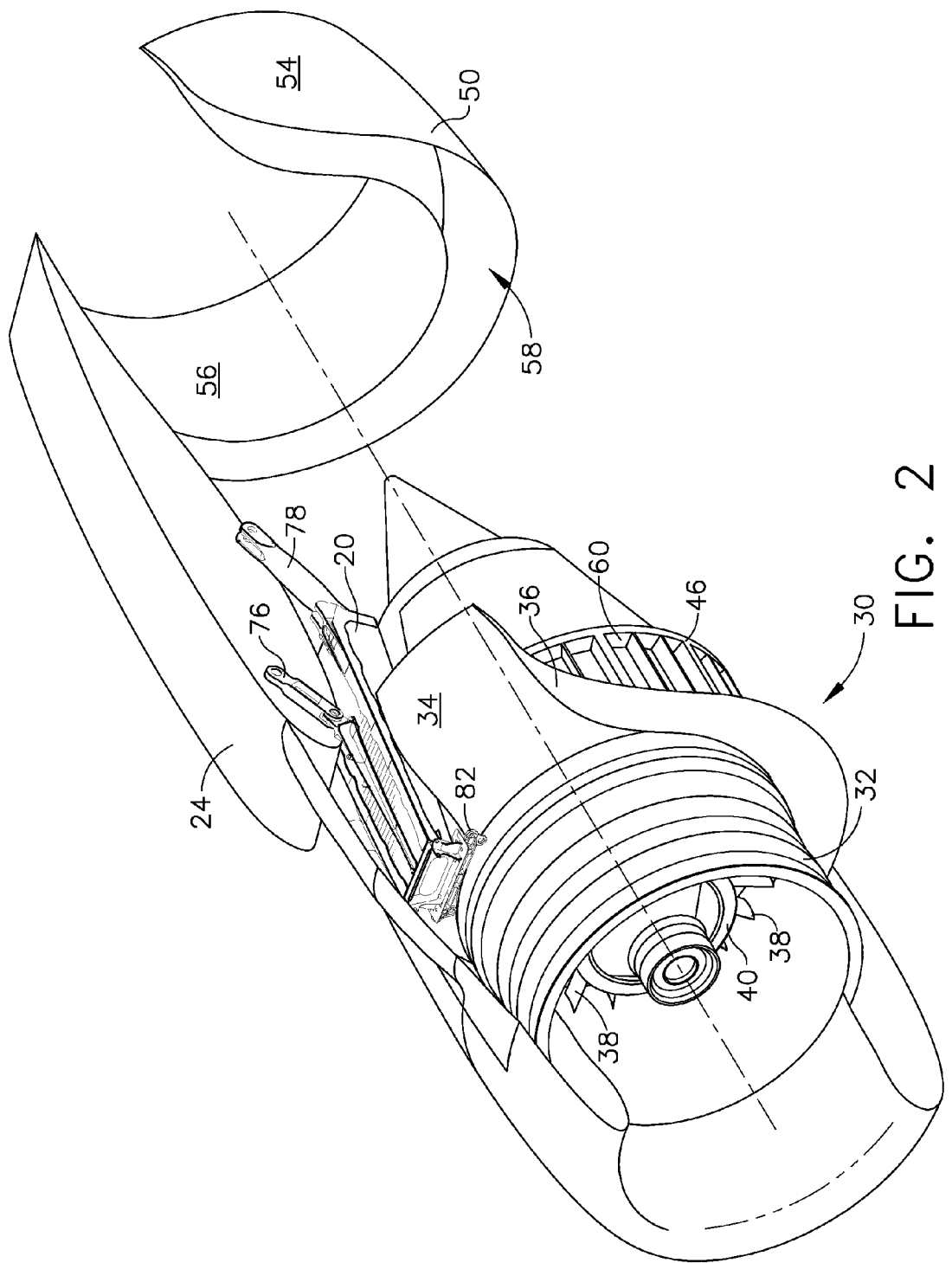
FIG. 2 is a perspective view of the exemplary assembly of FIG. 1, partially broken away, with showing a translatable cowl in a disengaged condition.

FIG. 2 illustrates a second exemplary integrated structure, termed herein as an integrated fan housing 30. The exemplary integrated fan housing 30 includes a fan case portion 32, a fan case extension 34, an aft bulkhead 36, a plurality of fan outlet guide vanes 38, and a fan hub portion 40. In an exemplary embodiment, the fan housing is fixedly secured at the fan case extension 34 to the support member. In an exemplary embodiment, static and dynamic loads may be distributed about the fan housing and into support member.

Exemplary embodiments disclosed herein include a thrust reversing assembly 44 (FIG. 1) including a cascade structure 46 in operative association with a translatable cowl 50, illustrated in a disengaged condition for the sake of clarity. The translatable cowl is sized and configured for cooperative engagement with the unitary nacelle structure 11 and integrated fan housing 30. The translatable cowl includes an outer skin 54 configured to cooperate with the nacelle structure 11 to provide an aerodynamic body when the translatable cowl 50 is in a forward, closed position. The translatable cowl 50 also includes an inner skin 56 configured to form an outer part of the bypass duct for fan air that is not directed through the engine core. The translatable cowl is rearwardly translatable, using suitable actuators or linkages (not shown), to provide an opening through which the bypass air may be directed during thrust-reversing operations. Generally, the outer and inner skins 54, 56 may be joined at the aft region, and separated at the forward region to provide a generally annular void 58. Cascade structure 46 is configured to be generally disposed in the void 58 when the translatable cowl 50 is in the closed position, is selectively uncovered by rearward translation of the translatable cowl from the closed position to a deployed position sufficient to uncover the cascade structure 46.

Figure 3:
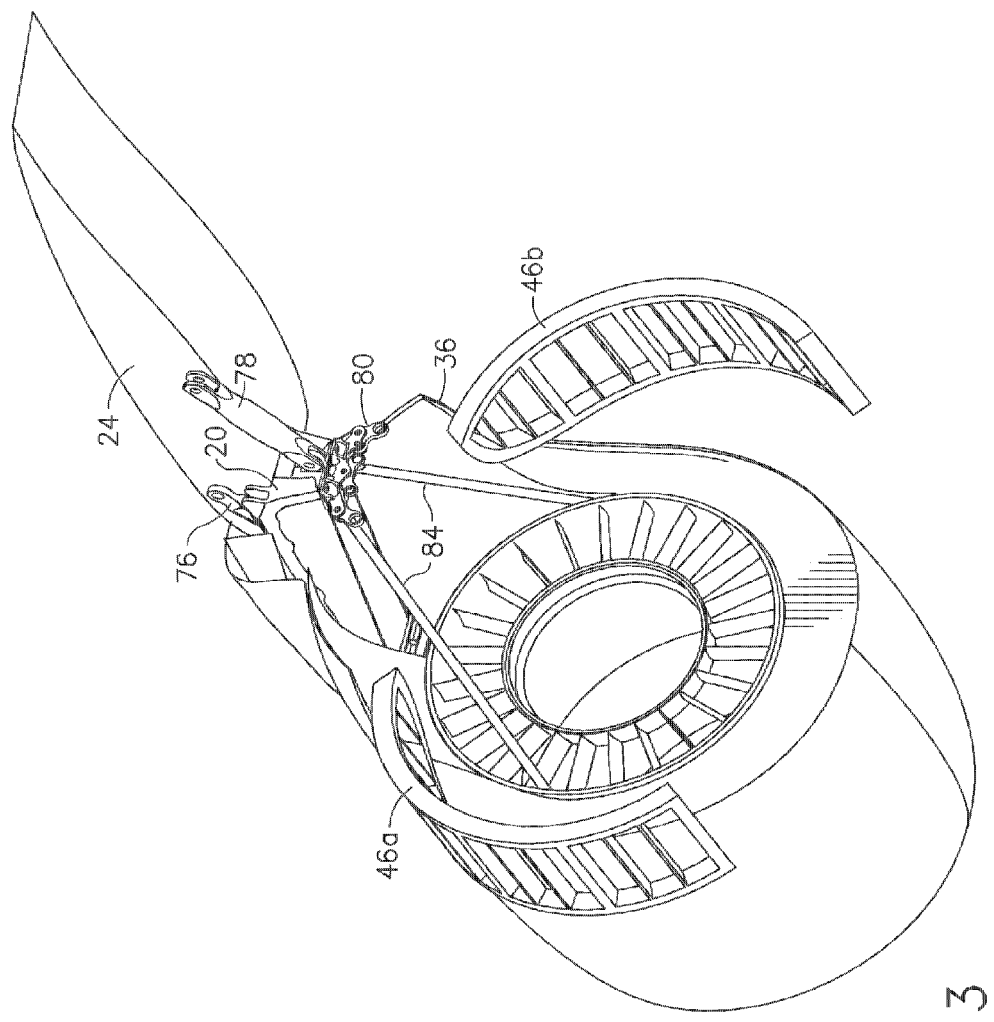
FIG. 3 is a perspective aft-looking forward view of certain structures of the exemplary engine assembly.

The cascade structure 46 defines a plurality of circumferentially arranged flow directing vents 60 for directing a flow of air generally outwardly and forwardly as is known in the art. With reference to FIG. 3, in an exemplary embodiment, the cascade structure 46 includes a pair of arcuate segments 46a, 46b carried in articulating relationship with the fan case aft bulkhead 36. Locking means or latches, such as those known in the art, may be provided to secure the arcuate segments during operational use.

In order to service the engine, the translatable cowl may be placed into the rearward, deployed position, or may be removed. The arcuate segments of the cascade structure may be unlatched and opened, clam-shell style, as illustrated in FIG. 3. Suitable holding mechanisms, such as rods or hooks, may be utilized to maintain the arcuate segments in an open position.

Figure 4:
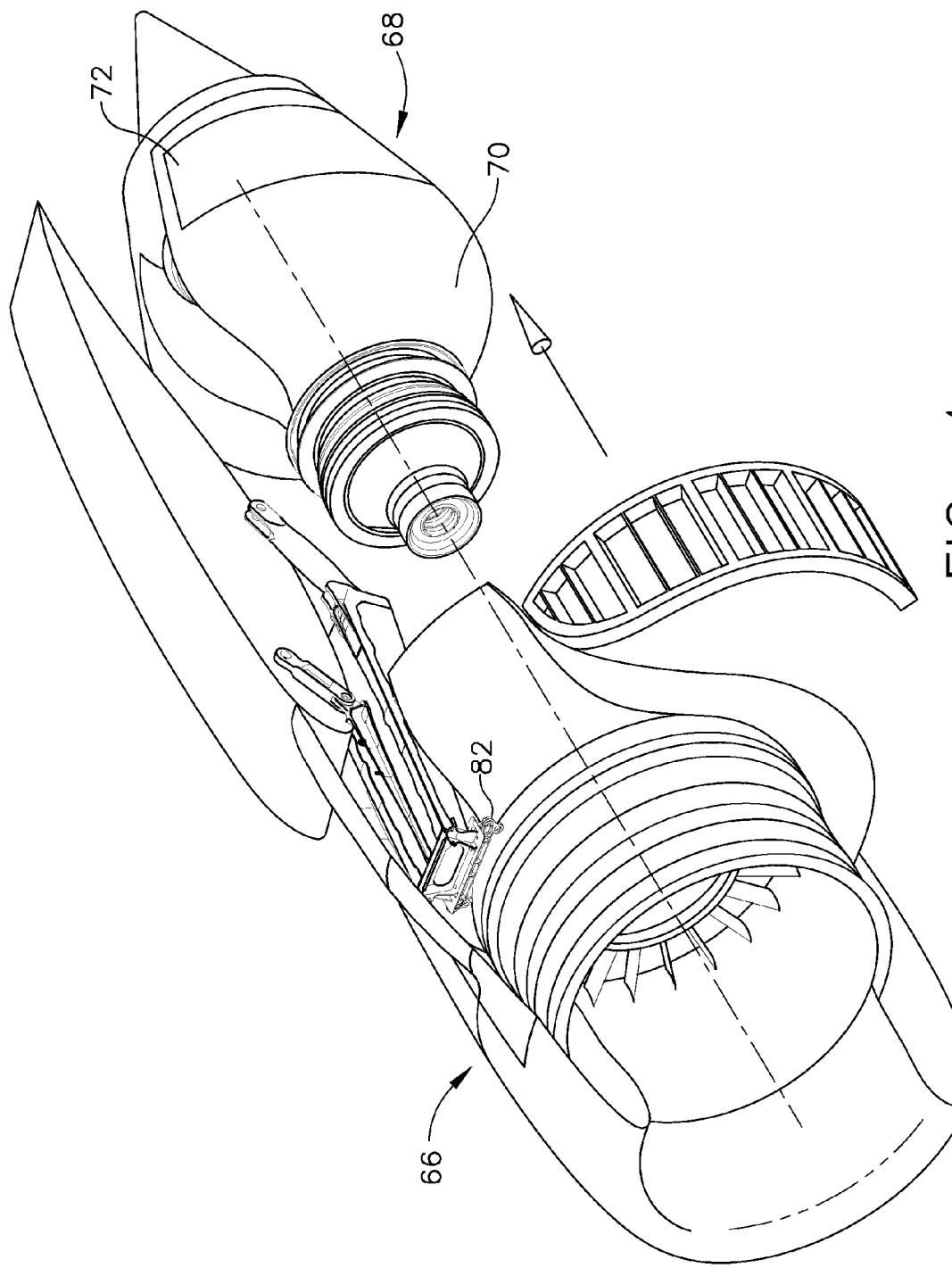
FIG. 4 is a shows a perspective view, similar to FIG. 2, in which an exemplary core engine module is illustrated in a disengaged condition.

An exemplary embodiment, illustrated in FIG. 4, includes a fan module, generally indicated 66 and a core engine module, generally indicated 68. During service opportunities, the core engine module 68 may be rearwardly displaced for removal (after removal of the fan blades, not shown). An exemplary core engine module 68 includes a core cowl 70 or case which forms an internal part of the by-pass duct. Core cowl 70 may include one or more movable panels 72 to facilitate maintenance of the core engine.

In an exemplary embodiment, with reference to FIGS. 1-4, various linkages, mounts and hangers are utilized to mount the engine assembly to the associated aircraft. For example, mid diagonal brace 76 and aft brace 78 extend between the support member 20 and wing 24. Aft engine hanger 80 selectively supports the core engine module 68. Forward hanger 82 supports and connects the integrated fan housing to the support member 20. Thrust links 84 serve to transfer thrust loads from the integrated fan housing 30 to the support member 20 and ultimately to the associated aircraft.

Exemplary embodiments disclosed herein provide integrated structures which cooperate to transmit static and dynamic forces directly a support structure rather than through the engine core to minimize backbone bending. The reduction in backbone bending allows for decreased clearances between rotatable parts and their respective shrouds or nozzles, thus improving engine efficiency. The lighter weight composite structures disclosed herein provide a weight benefit and further eliminate heavy joints. Exemplary arrangements of parts disclosed herein allow for easy installation and removal of the core engine module.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An assembly comprising:
    a unitary nacelle structure including an inlet region and a fan cowl region, wherein the unitary nacelle structure is configured to circumscribe at least a portion of an associated core engine module and to direct an airstream to a fan assembly driven by the core engine module;
    an integrated fan housing in supported connection with the unitary nacelle structure and at least partly disposed within the unitary nacelle structure, wherein the integrated fan housing comprises an integral composite structure and transmits static and dynamic loads directly to a support member adapted for mounting in supported connection with an aircraft to relieve backbone bending of the core engine module, the integral composite structure being integrally formed to include a fan case adapted to encircle the fan assembly of the core engine module and surrounded by the fan cowl region of the unitary nacelle structure, a fan hub that is surrounded by the fan case and is adapted to be located upstream of a core cowl of the core engine module and to receive and support the fan assembly of the core engine module, and a plurality of fan outlet guide vanes extending between and being formed with and directly connected to the fan case and the fan hub to form the integral composite structure; and
    mounts for fixedly securing the integrated fan housing to the support member.

2. The assembly according to claim 1 wherein the integral composite structure of the integrated fan housing further includes a fan case extension protruding from the fan case and extending aft of the fan case, and a fan case bulkhead unitary with the fan case and the fan case extension thereof.

3. The assembly according to claim 1 further comprising the support member, wherein the integrated fan housing further includes a fan case extension protruding from the fan case and extending aft of the fan case, and the fan case extension is attached to the support member for transmitting the static and dynamic loads to the support member.

4. The assembly according to claim 1 further comprising:
    a thrust reverser assembly including a translatable cowl sized and configured for cooperative engagement with the unitary nacelle structure to provide an aerodynamic body when the translatable cowl is in a forward position and to uncover a plurality of flow directing vents when the translatable cowl is in a deployed position.

5. The assembly according to claim 4 wherein the flow directing vents are circumferentially arranged on two arcuate cascade structures mounted in movable relationship to the integrated fan housing.

6. The assembly according to claim 1, the assembly further comprising the support member attached to the integrated fan housing and the core engine module mounted to the support member so that a portion of the core engine module is surrounded by the integrated fan housing, the fan case of the integrated fan housing encircles the fan assembly of the core engine module, and the fan hub receives and supports the fan assembly of the core engine module.

7. The assembly according to claim 6 wherein the core engine module includes an engine case and at least one movable access panel forming a part of the engine case.

8. An assembly adapted for use with an associated core engine module which drives a fan assembly that generates fan thrust loads, the assembly comprising:
    an integrated fan housing adapted to transmit the fan thrust loads directly to a support member mounted in supported connection with an aircraft to relieve backbone bending of the core engine module, the integrated fan housing comprising an integral composite structure, the integral composite structure being integrally formed to include:
        a fan case defining a generally cylindrical body being sized and configured for encircling the fan assembly of the core engine module;
        a fan hub that is surrounded by the fan case, the fan hub having an annular shape adapted to receive and support the fan assembly of the core engine module upstream of a core cowl of the core engine module;

a plurality of fan outlet guide vanes extending between and being formed with and directly connected to the fan hub and the fan case to form the integral composite structure; and mounts for fixedly securing the integrated fan housing to the support member.

9. The assembly according to claim 8, wherein the integral composite structure of the integrated fan housing further includes a fan case extension protruding from the fan case and extending aft of the fan case.

10. The assembly according to claim 9, wherein the integral composite structure of the integrated fan housing further includes a fan case bulkhead unitary with the fan case and the fan case extension thereof.

11. The assembly according to claim 10,
the assembly further comprising two arcuate cascade structures carried below the fan case extension in articulating relationship with the fan case bulkhead.

12. The assembly according to claim 1, wherein the unitary nacelle structure is a composite structure formed as a unitary member that includes the inlet region and the fan cowl region.

\* \* \* \* \*